(12) United States Patent
Wehrli

(10) Patent No.: US 8,299,274 B2
(45) Date of Patent: Oct. 30, 2012

(54) PROCESS FOR PRODUCING CARNOSOL FROM CARNOSIC ACID USING HYDROGEN PEROXIDE OR PERACIDS

(75) Inventor: Christof Wehrli, Witterswil (CH)

(73) Assignee: DSM IP Assets B.V., Heerlen (NL)

( * ) Notice: Subject to any disclaimer, the term of this patent is extended or adjusted under 35 U.S.C. 154(b) by 176 days.

(21) Appl. No.: 12/738,926

(22) PCT Filed: Oct. 21, 2008

(86) PCT No.: PCT/EP2008/008891

§ 371 (c)(1),
(2), (4) Date: Apr. 20, 2010

(87) PCT Pub. No.: WO2009/053026

PCT Pub. Date: Apr. 30, 2009

(65) Prior Publication Data

US 2010/0210859 A1      Aug. 19, 2010

(30) Foreign Application Priority Data

Oct. 22, 2007  (EP) .................................... 07020610
Nov. 21, 2007  (EP) .................................... 07022529
Apr. 15, 2008  (EP) .................................... 08007339
Sep. 30, 2008  (WO) ................. PCT/EP2008/008289

(51) Int. Cl.
*C07D 407/00* (2006.01)

(52) U.S. Cl. ...................................................... 549/278
(58) Field of Classification Search .................... 549/278
See application file for complete search history.

(56) References Cited

U.S. PATENT DOCUMENTS 4,450,097 A * 5/1984 Nakatani et al. .............. 252/404

FOREIGN PATENT DOCUMENTS

JP         2003-261454         9/2003

OTHER PUBLICATIONS

Marrero et al 2002 J. Natural Products 65:986-989.*
International Search Report for PCT/EP2008/008289, mailed Jan. 13, 2009.
Written Opinion of the International Searching Authority for PCT/EP2008/008289, mailed Jan. 13, 2009.
Masuda, T. et al., "Recover Mechanism of the Antioxidant Activity from Carnosic Acid Quinone, an Oxidized Sage and Rosemary Antioxidant", J. Agric. Food Chem., vol. 50, No. 21, (2002), pp. 5863-5869.
Masuda, T. et al., "Antioxidant Mechanism of Carnosic Acid: Structural Identification of Two Oxidation Products", Agric. Food Chem., vol. 49, No. 11, (2001), pp. 5560-5565.
Marrero, J.G. et al., "Semisynthesis of Rosmanol and its Derivatives, Easy Access to Abietatriene Diterpenes Isolated from the Genus *Salvia* with Biological Activities", J. Nat. Prod., vol. 65, No. 7, (2002), pp. 986-989.
Wenkert, E. et al., "Chemical Artifacts from the Family *Labiatae*", J. Org. Chem., vol. 30, (1965), pp. 2931-2934.
Database WPI, Derwent Publications Ltd., Accession No. 2003-884059 & JP 2003-261454, (Sep. 16, 2003).

* cited by examiner

*Primary Examiner* — Nizal Chandrakumar
(74) *Attorney, Agent, or Firm* — Nixon & Vanderhye P.C.

(57) ABSTRACT

Novel catalytic processes for the production of carnosol from carnosic acid using hydrogen peroxide or a peracid are presented. The carnosic acid may be in pure form, in an impure form, part of a plant extract, or may be present in rosemary needles. The catalyst may be iron, iron salts, a minor amount of water, rosemary needles, or a mixture thereof.

12 Claims, No Drawings

PROCESS FOR PRODUCING CARNOSOL FROM CARNOSIC ACID USING HYDROGEN PEROXIDE OR PERACIDS

This application is the U.S. national phase of International Application No. PCT/EP2008/008891 filed 21 Oct. 2008, which designated the U.S. and claims priority to EP Application No. 07020610.7 filed 22 Oct. 2007; EP Application No. 07022529.7 filed 21 Nov. 2007; EP Application No. 08007339.8 filed 15 Apr. 2008; and PCT/EP2008/008289 filed 30 Sep. 2008, the entire contents of each of which are hereby incorporated by reference.

BRIEF DESCRIPTION OF THE INVENTION

This invention relates to new processes for the production of carnosol from carnosic acid, which may be present in rosemary extract, rosemary needles, or in sage extracts using a catalyst and hydrogen peroxide or peracids.

BACKGROUND

Rosemary (*Rosmarinus officialis*) is a woody perennial herb with fragrant evergreen needle-like leaves native to the Mediterranean region. It is known as an herb commonly used in Mediterranean cuisine. Its dried form is high in iron, calcium and Vitamin B6. It also contains a carnosol, a polyphenol, which is an antioxidant and has recently been described as an anti-carcinogen (Lo et al 2002 *Carcinogenesis* 23(6): 983-991), working by suppressing the NF-κB pathway.

Lipophilic rosemary or sage extracts contain approximately 10-30% carnosic acid.

A process for synthesizing carnosol from carnosic acid was published by Marrero et al 2002 *J. Natural Products* 65:986-989. A "quantitative conversion" to carnosol is described whereby carnosic acid is dissolved in acetone and molecular oxygen was bubbled through the solution. However, despite numerous repetitions of this scheme, it was not repeatable, and virtually no carnosol was formed.

It would be desirable to have an easy, efficient process for transforming the carnosic acid into the biologically active form carnosol, especially if the extraction and transformation were essentially the same step.

DETAILED DESCRIPTION OF THE INVENTION

It has been found, in accordance with this invention, that carnosic acid can be converted into carnosol by an oxidation process which uses hydrogen peroxide or peracids as the oxygen source, provided that there is a catalyst present. The catalyst can either be: a catalytic amount of iron or iron salts, rosemary needles, or mixtures thereof. Choice of the catalyst will depend on other parameters of the reaction, which are presented in more detail below. Thus, one process of this invention comprises:
a) exposing carnosic acid to a solvent comprising a catalyst selected from the group consisting of minor amounts of iron, an iron salt, rosemary needles and mixtures thereof, and
b) introducing hydrogen peroxide or a peracid to produce carnosol.

While not wishing to be bound by theory, the conversion of carnosic acid is thought to occur in two stages. The first step is considered to be the oxidation to the quinone (although this has not yet been demonstrated by spectroscopy), followed by rearrangement to carnosol. The two stages may occur at same time or as discrete steps in a one-pot procedure, or may take place in separate reactions.

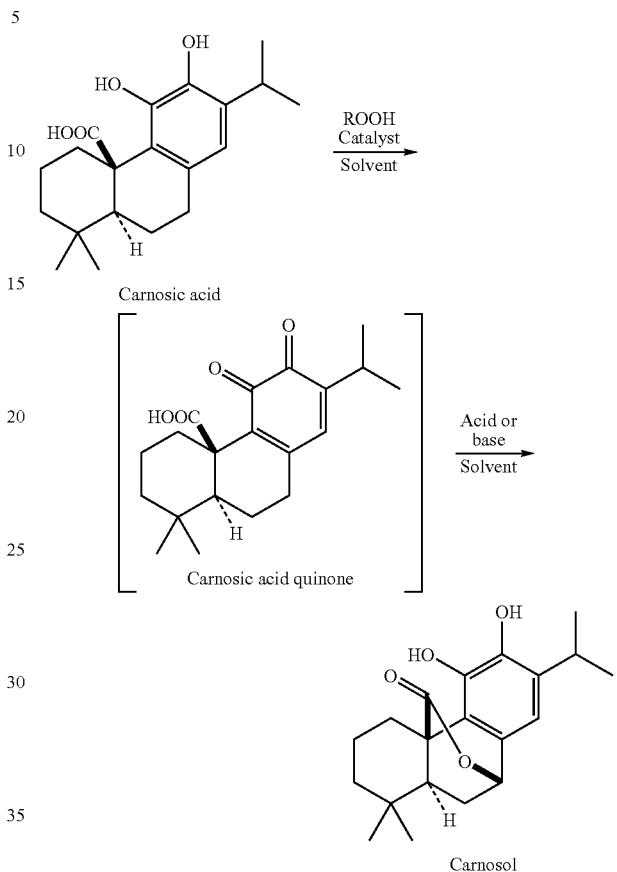

Also, in accordance with this invention, it has been found that the intermediate carnosic acid quinone can undergo rearrangement to produce carnosol in the presence of an acid or a weak base. Thus, this invention also comprises a process of producing carnosol from a carnosic acid quinone comprising exposing carnosic acid quinone to an acid or a weak base.

The carnosol-containing compositions produced by the reactions also form an embodiment of this invention. Thus this invention also comprises carnosol compositions made by any of the processes described herein, as well as to end products, such as nutraceuticals and pharmaceutical products which contain these carnosol-containing compositions.

The starting material for this reaction may be any source of carnosic acid. It may be purified carnosic acid itself, or carnosic acid which is not in a purified form, such as a rosemary extract or other plant extract which contains carnosic acid (such as sage, *Salvia* spp.). In another embodiment of the invention it may be rosemary leaves (needles). Many rosemary extracts are commercially available.

Optionally, the starting material may be subjected to a pretreatment step. In the pretreatment, the extract is treated with a solvent in the presence of charcoal. The preferred solvents are acetic acid, acetone, or methanol, with acetone as the most preferred. The amount of charcoal is not terribly critical, it may range from 1-100%, based on the weight of the rosemary extract. Preferred amounts are from 2-50%.

Catalysts

A. Oxidation Catalyst is Iron or Iron Salts:

It has been found, in accordance with this invention, that an iron catalyst, selected from the group consisting of iron, iron salts and mixtures thereof, acts as an oxidation catalyst, converting the carnosic acid to the intermediate quinone. Without the iron or iron salts, the oxidation of carnosic acid to the intermediate quinone is quite slow.

The iron salt may be any commonly used form of iron salts, (such as iron chloride, iron bromide, iron sulfate, iron acetate, iron citrate, iron gluconate, iron lactate, iron nitrates, iron hydroxides, and iron oxides, etc. or it may be already in the natural rosemary extract, as these extract usually already contain iron in unknown form. As used throughout the specification and claims, the term "iron salts" is intended to include both ferric salts and ferrous salts as well as the hydrates thereof.

If the solvent is acidic and stored in an iron container, the solvent will take up iron, and this amount is usually sufficient for purposes of this invention. The amounts of iron/iron salt needed are quite low: up to about 20 mole % (based on carnosic acid), with a preferred amount of from at least about 0.01 to 10 mole %, and more preferred from at least about 0.05 to 5 mole %. Higher amounts of iron may be present, of course; however in high amounts no particular advantage is seen.

B. Oxidation Catalyst is Rosemary Needles (Leaves)

In another embodiment of the invention, the rosemary needles themselves act as a catalyst during this extraction/conversion process.

Solvents

The solvents which can be used in the presence of an iron catalyst are virtually any solvent in which carnosic acid can be dissolved or is at least partially soluble. The solvent may be:

a neutral solvent, such as an ether (R2OR2 where R2, which may be the same or different, is C1 to C4), or
 an ester R1-COOR2 where R1 is H, or C1 to C3; and R2 is C1 to C4 (such as ethylacetate, butylacetate), or
 a ketone (such as acetone, methylethylketone or diethylketone) or
 dichloromethane, or
 an alcohol R2OH (such as ethanol, or isopropanol) where R2 is C1 to C4, or
 sub- or supercritical carbon dioxide "SF-CO2"; or
an acidic solvent having from 2 to 4 carbon atoms (such as acetic acid, propionic acid or isobutyric acid); or
 any mixture of the above solvents.

The preferred solvents are: dichloromethane, acetone, ethylacetate and acetic acid, propionic and isobutyric acid. The most preferred solvent is acetic acid, especially if the intended use of the carnosol is a food or pharmaceutical product.

Catalyst for the Transformation of the Intermediate Quinone

The carnosic acid in a solvent and a catalyst, is then reacted with hydrogen peroxide or a peracid.

In one embodiment, the oxidation reaction occurs either in the presence of a base or an acid. Alternatively, the base or the acid can also be added at a later stage of the oxidation, or after the formation of the intermediate quinone. In another alternative, the intermediate can be formed separately and then treated with an acid or base to form carnosol.

The base or the acid is believed to increase the rate of transformation of the intermediate, which is presumed to be a quinone.

For purposes of this reaction, the base can be present in any conveniently desired amount. If a base is chosen as a catalyst, then generally, the base will increase the reaction rate; i.e. the more base that is present, the faster the transformation will take place. Generally the base should be present in an amount of 0%-400 mole % based on the amount of carnosic acid. A preferred range is from about 10 to 300 mole %, and more preferably 80-200 mole %.

The choice of base will also be affected by the solvent chosen. In acidic solvent situations (i.e. SF-CO2, acetic acid, or other R-COOH), both strong and weak bases gave similar results. If an acidic solvent such as acetic acid is used, then in principle any base can be used, as all form the corresponding acetate. Thus, the base can be selected from the group consisting of: sodium- or potassium-(hydroxide, carbonate, hydrogen carbonate, acetate, propionate, phosphate); magnesium hydroxide, and mixtures thereof.

If the solvent used is a neutral one (such as dichloromethane, or ethylacetate) weak bases such as $NaHCO_3$, KOAc, $Na_2HPO_4$, and $Mg(OH)_2$ are preferred.

Preferred bases are generally Na- or K-hydrogen carbonate or acetate.

Alternatively, an acid can serve the same purpose as the base. If an acid is chosen as the catalyst, then virtually any strong acid can be used; mineral acids are preferred, such as: sulfuric acid, hydrochloric acid, hydrobromic acid, perchloric acid, nitric acid, or an sulfonic acid like p-toluenesulfonic acid. Most preferred is hydrochloric or hydrobromic acid. Generally the acid should be present in an amount of 0%-400 mole % based on the amount of carnosic acid. A preferred range is from about 5 to 200 mole %, and more preferably 20-100 mole % based on the amount of carnosic acid.

The use of acids as transformation catalysts is preferred in acidic solvents.

Oxidation Agent

Hydrogen peroxide or peracids can be used. For hydrogen peroxide any available source can be used such as hydrogen peroxide, sodium perborate, sodium percarbonate, hydrogen peroxide-urea or hydrogen peroxide in acetic acid. Hydrogen peroxide is preferred, such as commercial available hydrogen peroxide 30% or 50%.

As peracids, any commercial available peracid can be used, such as peracetic acid, perpropionic acid, albeit preferred is peracetic acid and most preferred are peracetic acid solutions in acetic acid.

Temperature—Regardless of Catalyst

In general, a higher temperature will result in a faster reaction. However, the reaction becomes less selective at higher temperatures. A preferred temperature range is from about 0°-100° C., a more preferred range is from about 10°-60° C., and an even more preferred range is from about 15°-40° C.

Optional Crystallization Step

Regardless of which of the above-described procedures are used, it is possible to increase the purity of the final carnosol obtained by subjecting the reaction product to a crystallization step. Crystallization may be accomplished using any conventional means; in most applications the preferred solvent is acetic acid. In some applications, crystals can be produced with a carnosol content exceeding 90%.

End Product Uses

The end product of these described reactions, while containing carnosol, also contain other reaction by-products. These compositions containing both carnosol and other reaction by-products hereinafter referred to as "carnosol process compositions", can be used directly without further purification or other processing in the use of foods and/or nutraceuticals for various uses.

The term "nutraceutical" as used herein denotes usefulness in both nutritional and pharmaceutical fields of application. Thus, novel nutraceutical compositions containing the carnosol process compositions can be used as supplements to food and beverages and as pharmaceutical formulations for enteral or parenteral application which may be solid formulations, such as capsules or tablets, or liquid formulations, such as solutions or suspensions.

The nutraceutical compositions according to the present invention may further contain protective hydrocolloids (such as gums, proteins, modified starches), binders, film-forming agents, encapsulating agents/materials, wall/shell materials, matrix compounds, coatings, emulsifiers, surface active agents, solubilising agents (oils, fats, waxes, lecithins etc.), adsorbents, carriers, fillers, co-compounds, dispersing agents, wetting agents, processing aids (solvents), flowing agents, taste-masking agents, weighting agents, jellifying agents, gel-forming agents, antioxidants and antimicrobials.

Moreover, a multi-vitamin and mineral supplement may be added to nutraceutical compositions of the present invention to obtain an adequate amount of an essential nutrient, which is missing in some diets. The multi-vitamin and mineral supplement may also be useful for disease prevention and protection against nutritional losses and deficiencies due to lifestyle patterns.

The nutraceutical compositions according to the present invention may be in any galenic form that is suitable for administering to the body, especially in any form that is conventional for oral administration, e.g. in solid forms such as (additives/supplements for) food or feed, food or feed premix, fortified food or feed, tablets, pills, granules, dragrées, capsules and effervescent formulations, such as powders and tablets, or in liquid forms, such as solutions, emulsions or suspensions as e.g. beverages, pastes and oily suspensions. The pastes may be incorporated in hard or soft shell capsules, whereby the capsules feature e.g. a matrix of (fish, swine, poultry, cow) gelatine, plant proteins or lignin sulfonate. Examples for other application forms are those for transdermal, parenteral or injectable administration. The dietary and pharmaceutical compositions may be in the form of controlled (delayed) release formulations.

Feed encompasses any feed given to pet animals, farm animals, animals used for the fur industry and aquaculture animals. It also encompasses treats given to pet animals (e.g. dogs and cats).

Examples of food are dairy products including, for example, margarines, spreads, butter, cheese, yoghurts or milk-drinks. Examples of fortified food are cereal bars, bakery items, such as cakes and cookies. Beverages encompass non-alcoholic and alcoholic drinks as well as liquid preparations to be added to drinking water and liquid food. Non-alcoholic drinks are e.g. soft drinks, sports drinks, fruit juices, lemonades, teas and milk-based drinks. Liquid foods are e.g. soups and dairy products. The nutraceutical composition containing carnosol process compositions may be added to a soft drink, an energy bar, or a candy, such that an adult consumes from about 10 to 1000 mg carnosol per daily serving, preferably from about 50 to 750 mg per daily serving, or more preferably from about 100 to 500 mg per daily serving.

If the nutraceutical composition is a pharmaceutical formulation the composition further contains pharmaceutically acceptable excipients, diluents or adjuvants. Standard techniques may be used for their formulation, as e.g. disclosed in *Remington's Pharmaceutical Sciences*, 20th edition Williams & Wilkins, Pa., USA. For oral administration, tablets and capsules are preferably used which contain a suitable binding agent, e.g. gelatine or polyvinyl pyrrolidone, a suitable filler, e.g. lactose or starch, a suitable lubricant, e.g. magnesium stearate, and optionally further additives.

The nutraceuticals can be used to maintain or improve various conditions, such as for its anti-inflammation properties, to maintain or improve mind or mood and for joint health.

The following non-limiting Examples are presented to better illustrate the invention.

Example 1

Control Experiment

A solution of 0.132 g carnosic acid (content=90% carnosic acid, 2% carnosol) in 30 ml acetone was stirred in a 10 ml reaction vessel at ambient in an atmosphere of oxygen for 23 h. These are essentially the conditions described in J. G. Marrero, L. S. Andres, J. G. Luis; *J. Nat. Prod.* (2002), 65, 986-989. The solution contained: 88% carnosic acid, and only 3% carnosol.

Example 2

18.5 g rosemary extract (containing 40% carnosic acid and 4% carnosol), 55 g acetic acid and 7 mg of iron(III) chloride hexahydrate where stirred under a nitrogen blanket. At 15° C. was slowly added 4.7 ml peracetic acid 32% in acetic acid. The mixture was stirred for 2 h at 15° C. 1 ml hydrochloric acid 37% in water was added and the mixture was stirred for 18 h. The suspension was filtered and washed with 10 ml acetic acid. The crystals where dried in the vacuum at 70° C. We obtained 5.68 g carnosol of 88% purity. Yield=62%.

Example 3

13.1 g rosemary extract (containing 43% carnosic acid and 18% carnosol), 60 g acetic acid and 13 mg of iron(III) chloride hexahydrate where stirred under a nitrogen blanket. At 15° C. was slowly added 2.9 ml hydrogen peroxide 35% in water. The mixture was stirred for 1.5 h at 15° C. followed by addition of 1 ml hydrochloric acid 37%. The mixture was stirred for 18 h at ambient. The slurry was filtered and washed with 10 ml acetic acid. The crystallisate was dried in the vacuum at 70° C. We obtained 5.57 g carnosol of 92% purity. Yield=65%.

Example 4

13.1 g rosemary extract (containing 43% carnosic acid and 18% carnosol), 60 g acetic acid, 2.5 g sodium acetate and 7 mg of iron(III) chloride hexahydrate where stirred under a nitrogen blanket. At 18° C. was slowly added 2.9 ml hydrogen peroxide 35% in water. The mixture was stirred for 21 h at ambient. The slurry was filtered and washed with 10 ml acetic acid. The crystallisate was dried in the vacuum at 70° C. We obtained 4.24 g carnosol of 86% purity. Yield=45%.

Example 5

7.6 g rosemary extract (containing 40% carnosic acid and 3.5% carnosol), 23 g acetic acid, 0.4 ml hydrochloric acid 37% and 5.2 mg of iron(III) chloride hexahydrate was stirred under a nitrogen blanket. At 15° C. was slowly added 0.90 ml hydrogen peroxide 50% in water. The mixture was stirred for 4 h at 18° C. The mixture was analysed by HPLC for content of carnosol. Yield=90%.

Example 6

10.7 g rosemary extract (containing 15% carnosic acid and 16% carnosol), 32 g acetic acid, 0.2 ml hydrochloric acid 37% and 5.2 mg of iron(III) chloride hexahydrate was stirred under a nitrogen blanket. At 18° C. was slowly added 0.54 ml hydrogen peroxide 50% in water. The mixture was stirred for 3 h at ambient. The mixture was analysed by HPLC for content of carnosol. Yield=80%.

Example 6

7.6 g rosemary extract (containing 40% carnosic acid and 3.5% carnosol) and 0.76 g charcoal where stirred in 32 ml acetone at reflux for 10 minutes, cooled to ambient and filtered. The charcoal was washed with 8 ml acetone. The filtrate was evaporated to dryness. To the residue was added 22 g acetic acid, 0.4 ml hydrochloric acid 37% and 7.2 mg of iron(III) chloride hexahydrate. The mixture was stirred under a nitrogen blanket. At 18° C. was slowly added 0.90 ml hydrogen peroxide 50% in water. The mixture was stirred for 5 h at ambient. The slurry was filtered and washed with 10 ml acetic acid. The crystallisate was dried in the vacuum at 70° C. We obtained 2.61 g carnosol of 88% purity. Isolated yield=70%

Example 7

7.6 g rosemary extract (containing 40% carnosic acid and 3.5% carnosol) and 0.76 g charcoal where stirred in 32 ml acetone at reflux for 10 minutes, cooled to ambient and filtered. The charcoal was washed with 8 ml acetone. The filtrate was evaporated to dryness. To the residue was added 23 g acetic acid, 0.4 ml hydrochloric acid 37%. The mixture was stirred under a nitrogen blanket. At 18° C. was slowly added 0.90 ml hydrogen peroxide 50% in water. The mixture was analysed by HPLC for content of carnosol. Yield=83%

What is claimed is:

1. A process for converting carnosic acid to carnosol comprising the steps of:
    a) exposing carnosic acid to a solvent comprising a catalyst selected from the group consisting of minor amounts of water, iron, iron salt, rosemary needles and mixtures thereof, and
    b) introducing an oxidation agent selected from the group consisting of hydrogen peroxide and a source of hydrogen peroxide to produce carnosol.

2. A process according to claim 1 wherein the carnosic acid is present in a plant extract.

3. A process according to claim 2 wherein the plant extract is rosemary extract.

4. A process according to claim 1 wherein the oxidation agent is introduced in the presence of a base or an acid.

5. A process according to claim 1 wherein the base or an acid is introduced after the oxidation agent.

6. A process according to claim 1 wherein the oxidation agent is from a source of hydrogen peroxide selected from the group consisting of sodium perborate, sodium percarbonate and hydrogen peroxide-urea.

7. A process according to claim 1 wherein the oxidation agent is hydrogen peroxide.

8. A process according to claim 1 wherein the iron salts are selected from the group consisting of: ferric salts and ferrous salts of iron chloride, iron bromide, iron sulfate, iron nitrate, iron acetate, iron propionate, iron citrate, iron gluconate, iron lactates, iron oxides, iron hydroxides, hydrates thereof, and mixtures thereof.

9. A process according to claim 1 wherein the solvent is selected from the group consisting of: an acidic solvent $R1$-COON where $R1$ is $C1$ to $C3$, a neutral solvent, an ether ($R2OR2$ where $R2$, which may be the same or different, is $C1$ to $C4$), an ester ($R1$-COOR2 where $R1$ is H, or $C1$ to $C3$; and $R2$ is $C1$ to $C4$) (such as ethylacetate, butyl acetate), or a ketone, dichloromethane, an alcohol $R2OH$ where $R2$ is $C1$ to $C4$, sub- or supercritical carbon dioxide "SF-CO2"; and any mixture of the above solvents.

10. A process according to claim 9 wherein the solvent is selected from the group consisting of: a carbonic acidic solvent having from 2 to 4 carbon atoms or mixtures thereof.

11. A process according to claim 10 wherein the solvent is acetic acid.

12. A process according to claim 2, further comprising, prior to step a), pretreating the plant extract with charcoal in the presence of a solvent selected from the group consisting of acetic acid, acetone, and methanol.

* * * * *